United States Patent
Buttermann

(10) Patent No.: US 9,775,650 B2
(45) Date of Patent: Oct. 3, 2017

(54) SCREW CLAMP ORTHOPEDIC DEVICE AND METHODS OF IMPLEMENTATION

(71) Applicant: Dynamic Spine, LLC, Mahtomedi, MN (US)

(72) Inventor: Glenn R. Buttermann, Mahtomedi, MN (US)

(73) Assignee: Dynamic Spine, LLC, Mahtomedi, MN (US)

( * ) Notice: Subject to any disclaimer, the term of this patent is extended or adjusted under 35 U.S.C. 154(b) by 49 days.

(21) Appl. No.: 14/772,546

(22) PCT Filed: Mar. 10, 2014

(86) PCT No.: PCT/US2014/022579
§ 371 (c)(1),
(2) Date: Sep. 3, 2015

(87) PCT Pub. No.: WO2014/164490
PCT Pub. Date: Oct. 9, 2014

(65) Prior Publication Data
US 2016/0015430 A1  Jan. 21, 2016

Related U.S. Application Data

(60) Provisional application No. 61/776,308, filed on Mar. 11, 2013.

(51) Int. Cl.
*A61B 17/70* (2006.01)

(52) U.S. Cl.
CPC ...... *A61B 17/7047* (2013.01); *A61B 17/7002* (2013.01); *A61B 17/707* (2013.01);
(Continued)

(58) Field of Classification Search
CPC .......................... A61B 17/707; A61B 17/7001
See application file for complete search history.

(56) References Cited

U.S. PATENT DOCUMENTS 4,422,451 A * 12/1983 Kalamchi .......... A61B 17/7002
606/207
5,263,954 A * 11/1993 Schlapfer .......... A61B 17/7056
606/1
(Continued)

FOREIGN PATENT DOCUMENTS

JP        11-347046 A    12/1999
WO   WO-2012/062879 A1   5/2012

OTHER PUBLICATIONS

Supplementary European Search Report in corresponding European Application No. 14 77 9671 dated Oct. 21, 2016, 8 pages.
(Continued)

*Primary Examiner* — Ellen C Hammond
*Assistant Examiner* — Stuart S Bray
(74) *Attorney, Agent, or Firm* — Foley & Lardner LLP

(57) ABSTRACT

A screw-clamp apparatus is disclosed that includes a first clamp component comprising at least one hook, a second clamp component comprising at least one hook, a bone-screw hole located on the first clamp component, a bone screw configured to be inserted through the bone-screw hole and to be inserted into bone and a spacer-receiver located on the first clamp component. The second clamp component can be pivotably attached relative to the first clamp component. A portion of the bone screw can be configured to engage the second clamp component upon insertion to cause the second clamp component to pivot toward the first clamp component. The spacer-receiver can be configured to secure a spacer.

16 Claims, 17 Drawing Sheets

(52) U.S. Cl.
CPC ...... *A61B 17/7014* (2013.01); *A61B 17/7032* (2013.01); *A61B 17/7056* (2013.01)

(56) References Cited

U.S. PATENT DOCUMENTS

| | | | | |
|---|---|---|---|---|
| 5,304,179 | A * | 4/1994 | Wagner | A61B 17/7007 403/371 |
| 5,380,326 | A * | 1/1995 | Lin | A61B 17/7032 403/13 |
| 5,437,669 | A * | 8/1995 | Yuan | A61B 17/7047 606/264 |
| 5,630,816 | A * | 5/1997 | Kambin | A61B 17/701 606/251 |
| 5,688,273 | A * | 11/1997 | Errico | A61B 17/7056 606/276 |
| 7,666,210 | B2 * | 2/2010 | Franck | A61B 17/7052 606/250 |
| 8,114,130 | B2 * | 2/2012 | Winslow | A61B 17/7035 606/246 |
| 8,298,275 | B2 * | 10/2012 | Rezach | A61B 17/7032 606/267 |
| 8,790,380 | B2 * | 7/2014 | Buttermann | A61B 17/7047 606/324 |
| 8,915,962 | B1 * | 12/2014 | Suddaby | A61B 17/1637 623/17.11 |
| 2005/0228377 | A1 * | 10/2005 | Chao | A61B 17/7052 606/252 |
| 2006/0095035 | A1 * | 5/2006 | Jones | A61B 17/7037 606/57 |
| 2007/0072459 | A1 * | 3/2007 | Stahurski | A61B 17/7032 439/135 |
| 2007/0118122 | A1 * | 5/2007 | Butler | A61B 17/7023 606/86 A |
| 2007/0156143 | A1 * | 7/2007 | Lancial | A61B 17/7032 606/250 |
| 2007/0161994 | A1 * | 7/2007 | Lowery | A61B 17/7032 606/86 A |
| 2007/0213719 | A1 * | 9/2007 | Hudgins | A61B 17/8004 606/278 |
| 2007/0233068 | A1 * | 10/2007 | Bruneau | A61B 17/7067 623/17.11 |
| 2007/0233090 | A1 * | 10/2007 | Naifeh | A61B 17/7023 606/258 |
| 2007/0233091 | A1 * | 10/2007 | Naifeh | A61B 17/7005 606/279 |
| 2007/0233094 | A1 * | 10/2007 | Colleran | A61B 17/7007 606/86 A |
| 2007/0244481 | A1 * | 10/2007 | Timm | A61B 17/7007 606/250 |
| 2007/0250061 | A1 * | 10/2007 | Chin | A61B 17/7001 606/86 A |
| 2007/0270819 | A1 * | 11/2007 | Justis | A61B 17/701 606/279 |
| 2007/0270837 | A1 * | 11/2007 | Eckhardt | A61B 17/7004 606/279 |
| 2009/0270929 | A1 * | 10/2009 | Suddaby | A61B 17/1637 606/324 |
| 2010/0137913 | A1 * | 6/2010 | Khatchadourian | A61B 17/7014 606/258 |
| 2010/0217271 | A1 * | 8/2010 | Pool | A61B 17/7004 606/90 |
| 2010/0222822 | A1 * | 9/2010 | Farris | A61B 17/7004 606/264 |
| 2010/0274291 | A1 * | 10/2010 | McClellan, III | A61B 17/7004 606/276 |
| 2011/0137353 | A1 * | 6/2011 | Buttermann | A61B 17/7001 606/305 |
| 2013/0231704 | A1 * | 9/2013 | Larroque-Lahitette | A61B 17/7056 606/277 |
| 2013/0274807 | A1 * | 10/2013 | Prajapati | A61B 17/7049 606/278 |
| 2013/0304129 | A1 * | 11/2013 | Hawkins | A61B 17/7056 606/276 |
| 2014/0222074 | A1 * | 8/2014 | Rathbun | A61B 17/7014 606/258 |
| 2014/0277147 | A1 * | 9/2014 | Alexander | A61B 17/7014 606/259 |
| 2014/0343612 | A1 * | 11/2014 | Rezach | A61B 17/7032 606/276 |
| 2014/0350602 | A1 * | 11/2014 | Seme | A61B 17/70 606/250 |
| 2015/0032158 | A1 * | 1/2015 | Khajavi | A61B 17/7049 606/246 |
| 2015/0032159 | A1 * | 1/2015 | Beger | A61B 17/8605 606/265 |

OTHER PUBLICATIONS

International Search Report in PCT/US2014/022579 dated Jul. 21, 2014.
International Preliminary Report on Patentability in PCT/US2014/022579 mailed Sep. 24, 2015, 9 pages.

* cited by examiner

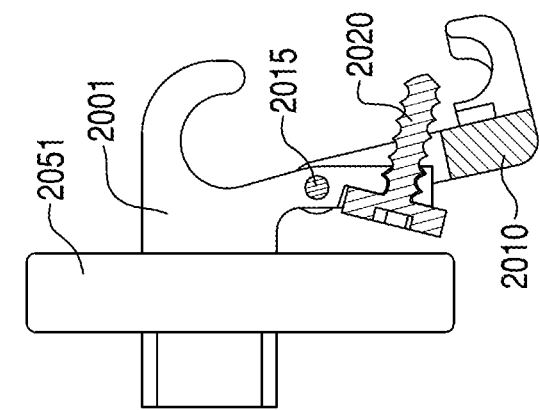
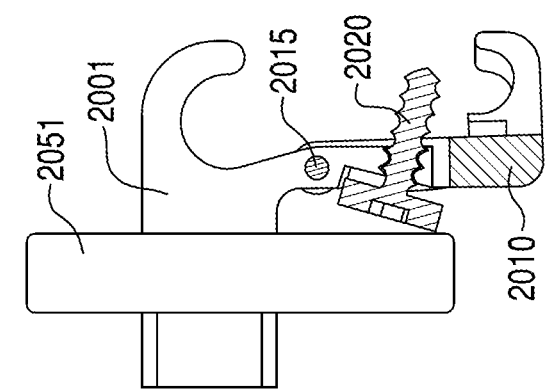
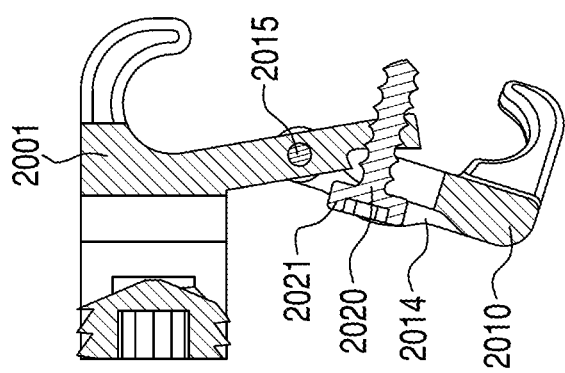

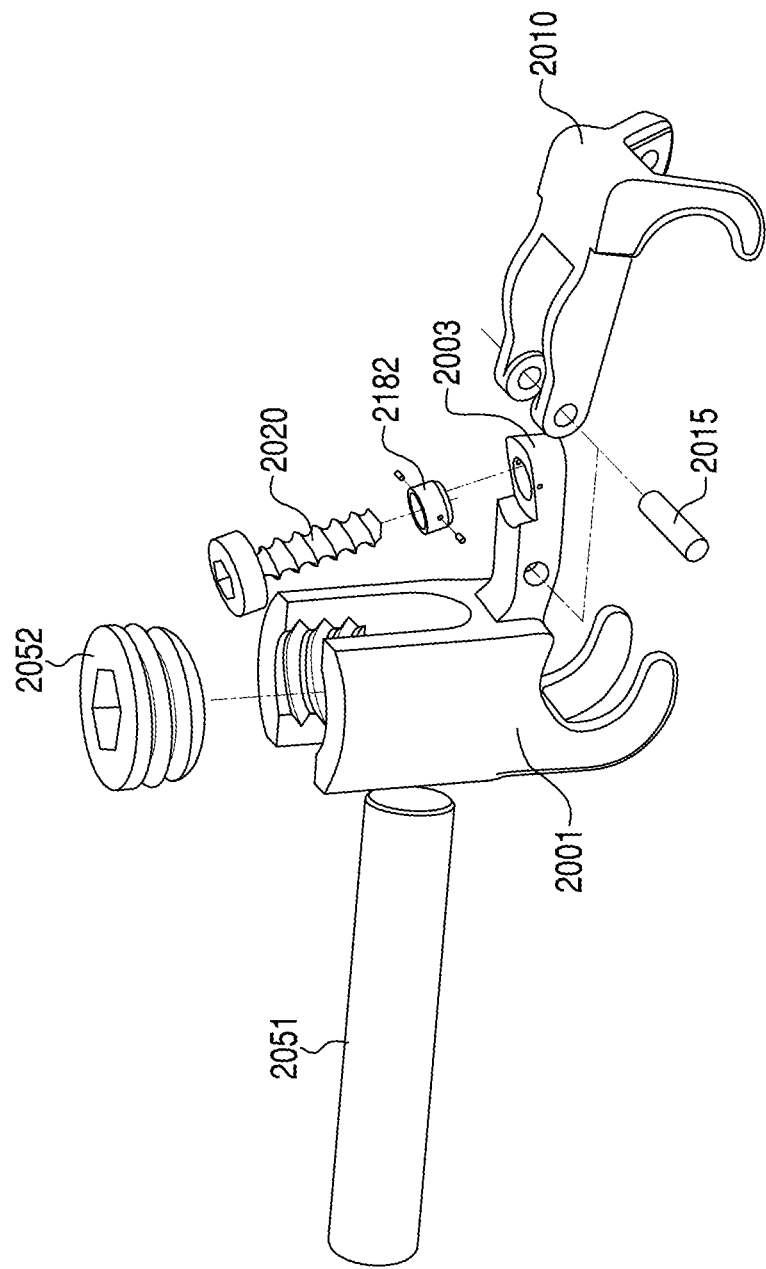

SCREW CLAMP ORTHOPEDIC DEVICE AND METHODS OF IMPLEMENTATION

CROSS-REFERENCE TO RELATED PATENT APPLICATIONS

The present application is a U.S. National Stage of International Application No. PCT/US2014/022579 filed on Mar. 10, 2014, which claims the benefit of U.S. Provisional Patent Application No. 61/776,308 filed on Mar. 11, 2013, the entire disclosures of all of which are incorporated herein by reference.

TECHNICAL FIELD

The presently disclosed embodiments relate generally to a screw-clamp device or apparatus and methods of implementing the same. The presently disclosed embodiments relate generally to orthopedic devices.

BACKGROUND

Due to the unique anatomy of the posterior thoracic spine, providing instrumentation for applying corrections to the spine, through for example fusion devices, presents numerous challenges. Some instrumentation for engaging in various spinal corrective procedures includes nonsegmental hook constructs, such as Harrington rods. The implementation of these rods has potential adverse results, such as flat-back deformity, hook pull out or dislodgement and high nonunion rates. Other hook constructs, such as Cotrel-Dubosset, allow for segmental fixation and better curve correction and control; however, these constructs cause a relatively high pseudoarthrosis rate to occur due to the large number of hooks displacing bone grafts, which are required with these constructs for biological fusion to take place. Such systems have also proven to be exceptionally difficult to remove or revise. Hybrid constructs may be implemented that use pedicle screw instrumentation in the distal thoracic spine and hook fixation or sublaminar wire fixation in the proximal and midthoracic spine, but are still complicated by the aforementioned issues related to the hook and screw implementation described.

Thoracic pedicle screw instrumentation implementation has increased due to the increase in construct rigidity and scoliosis correction. Pedicle screw constructs may have a risk of neurological or vascular injury if they are misplaced. Studies have found that the more proximal screws were at greater risk of malposition where the pedicles may have abnormal morphology. Other studies have found that on average over 12% of screws were misplaced of which half of those were of concern (adjacent or impinging the aorta or other viscera, or within the spinal canal adjacent or impinging the spinal cord). To overcome the risks of thoracic pedicle screw instrumentation, some authorities suggest the use of intraoperative CT scans. Successful image guidance navigation systems may need to visualize the entire thoracic spine during deformity surgery. This typically requires 4 or 5 intraoperative CT scans for a typical patient. The relatively high radiation exposure of multiple CT scans, when used in various patients such as the typical female adolescent, is a concern as this is the time when these patients are at greatest risk for radiation induced breast or other cancers given that they are still growing and unshielded.

In elderly patients or adults with osteoporosis, pedicle screw constructs have a potential risk of screw pullout and may need augmentation with bone cement. Some spine surgeons may opt to use sublaminar wires or hook instrumentation at the end vertebra to reinforce the pedicle screws. However, even well placed screws are a risk for osteoporosis patients due to the potential of "plowing" of the pedicle screws out of the pedicles and subsequently affecting the adjacent vascular structures.

Another potential problem in deformity patients treated with pedicle screw constructs is an increased risk for proximal junctional kyphosis, PJK. There is a loss of thoracic kyphosis associated with thoracic pedicle screw constructs. Chronic PJK may be secondary to this iatrogenic thoracic lordosis as the spine tries to balance itself in patients treated with screw constructs.

SUMMARY

According to one embodiment, a screw-clamp apparatus may include a first clamp component comprising at least one hook, a second clamp component comprising at least one hook, a bone-screw hole located on the first clamp component, a bone screw configured to be inserted through the bone-screw hole and to be inserted into bone and a spacer-receiver located on the first clamp component. The second clamp component can be pivotably attached relative to the first clamp component. A portion of the bone screw can be configured to engage the second clamp component upon insertion to cause the second clamp component to pivot toward the first clamp component. The spacer-receiver can be configured to secure a spacer.

According to another embodiment, at least one of the first clamp component and the second clamp component of the screw-clamp apparatus may optionally have a protruding or prominent portion, shoulder, or cam, wherein a force applied onto the protruding portion by a bone screw-head of the bone screw may pivot the second clamp component toward the first clamp component.

According to another embodiment, an orthopedic device to realign bone segments, may include at least two screw-clamp apparatus and a spacer connecting the at least two screw-clamp apparatus along a lengthwise direction of a spine. The at least two screw-clamp apparatus may comprise first clamp component comprising at least one hook, a second clamp component comprising at least one hook, a bone screw configured to be inserted into the first clamp component and into bone, and a spacer-receiver located on the first clamp component. The second clamp component can be pivotably attached relative to the first clamp component. A portion of the bone screw can be configured to engage the second clamp component upon insertion to cause the second clamp component to pivot toward the first clamp component. The spacer can be removably secured within the spacer-receivers.

According to another embodiment, a method of assembling a screw-clamp apparatus may include pivotally attaching a first clamp component comprising at least one hook to a second clamp component comprising at least one hook, inserting a bone screw into a bone-screw hole located on the first clamp component, engaging the bone screw along the second clamp component to cause the second clamp component to pivot toward the first clamp component, and attaching a spacer to a spacer-receiver located on the first clamp component.

BRIEF DESCRIPTION OF THE DRAWINGS

These and other features, aspects, and advantages of the present invention will become apparent from the following description, appended claims, and the accompanying exemplary embodiments shown in the drawings, which are briefly described below.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 8A-8C illustrate partial cut away, side views of the screw-clamp device of FIG. 5 in various positions related to transitioning from an open state to a closed state as a screw is tightened within the screw-clamp device, in accordance with an exemplary embodiment.

FIG. 9 provides an exploded, perspective view of the screw-clamp device of FIG. 5 with a connecting rod, in accordance with an exemplary embodiment.

The features and advantages of the inventive concepts disclosed herein will become more apparent from the detailed description set forth below when taken in conjunction with the drawings.

DETAILED DESCRIPTION

Following below are more detailed descriptions of various concepts related to, and embodiments of, inventive apparatuses and methods for a screw-clamp apparatus. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Referring generally to the Figures, various embodiments of a screw-clamp apparatus are shown. Inventive embodiments illustrated and described herein act as a "claw" to the lateral mass of the thoracic vertebra. Various embodiments of the screw-clamp apparatus or device allow the ease of use that may be associated with hooks but give rigidity akin to that of a pedicle screw without the same level of risks of injury to the spinal cord, aorta, adjacent viscera or risk of pullout in osteoporotic patients. The present invention may be used to realign or straighten the spine. For example, the screw-clamp apparatus may be used to treat and correct orthopedic and/or spinal defects, like scoliosis, which is the side-to-side or lateral curvature of the spine.

Figure 1A:
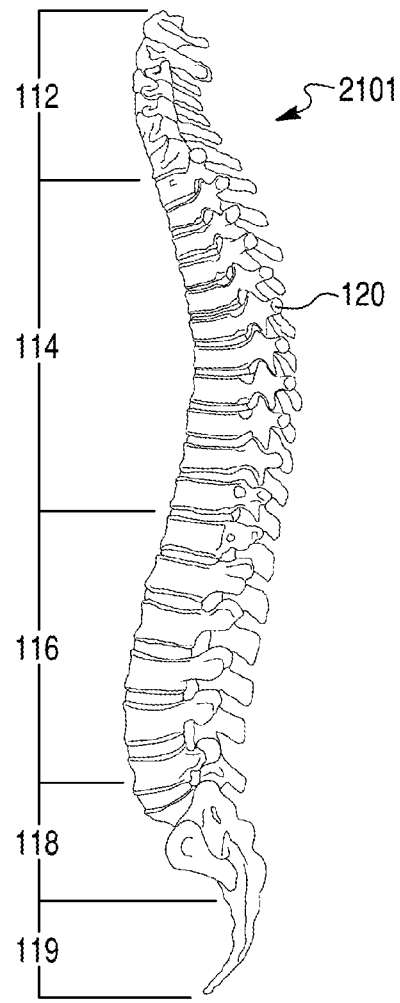
FIGS. 1A and 1B are side and front views of a human spine.
Figure 1B:
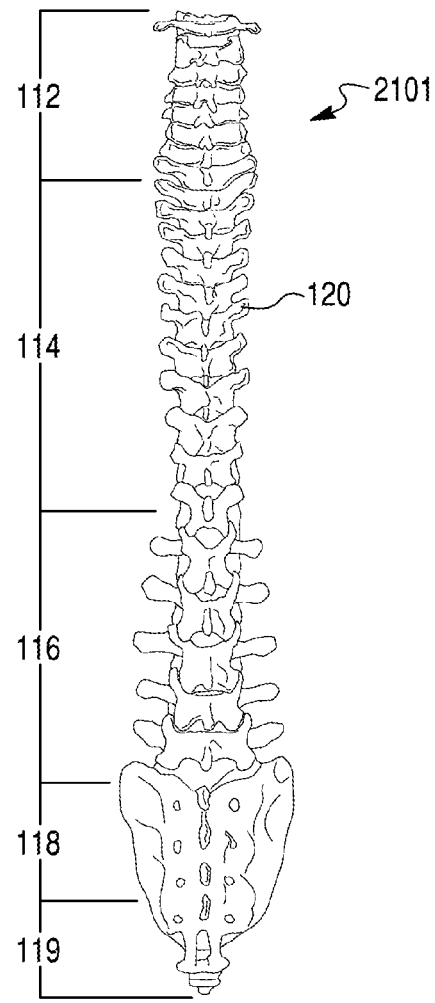

As shown in FIGS. 1A and 1B, the spine 2101 of the human body is categorized into five regions of vertebrae 120. The cervical vertebrae 112 (including vertebrae C1-C7) generally comprises the neck region of the spine and is connected to the base of the skull. The thoracic vertebrae 114 (including vertebrae T1-T12) generally comprises the upper back region of the spine. The lumbar vertebrae 116 (including vertebrae L1-L5) generally comprises the lower back region of the spine. The sacrum 118 and coccyx 119 generally comprise the lowermost portion of the spine and the tailbone and include fused vertebrae.

Figure 2:
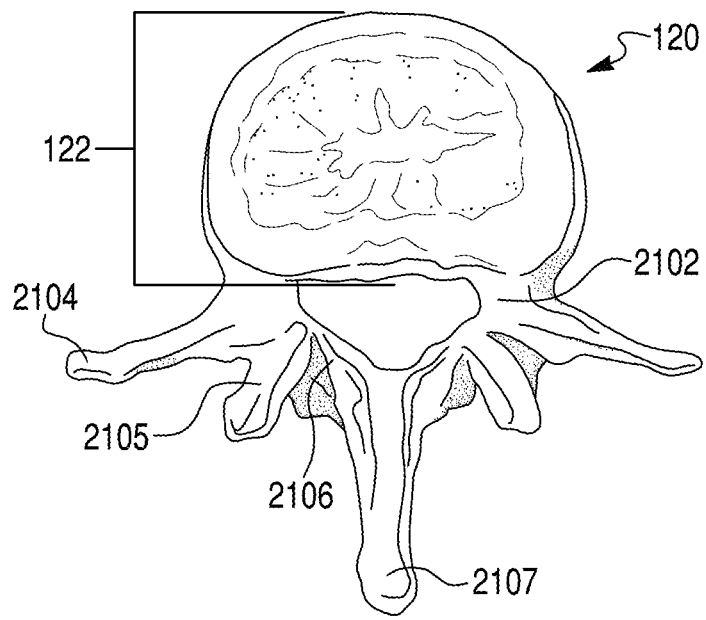
FIG. 2 is a top view of a human vertebrae from the spine of FIG. 1A.
Figure 3:
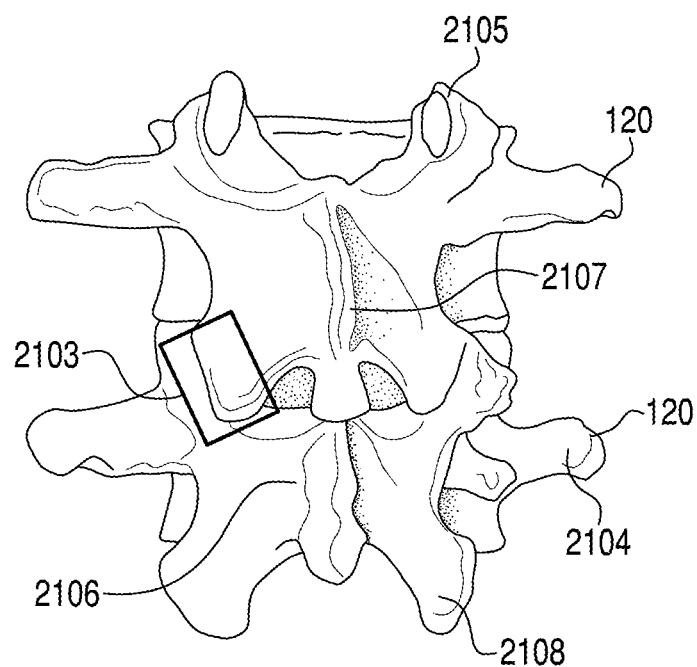
FIG. 3 is a back view of two human vertebrae from the spine of FIG. 1A.

As shown in FIGS. 2 and 3, a vertebrae 120 of the spine 2101 may include multiple different regions or bones. The body 122 of the vertebrae 120 may at least partially support the various components of the vertebrae 120. For example, the vertebrae 120 may include a facet joint 2103, a transverse process 2104, a superior articular process 2105, a lamina 2106, a spinous process 2107, inferior articular process 2108, a lateral mass, and a pedicle 2102.

Figure 4:
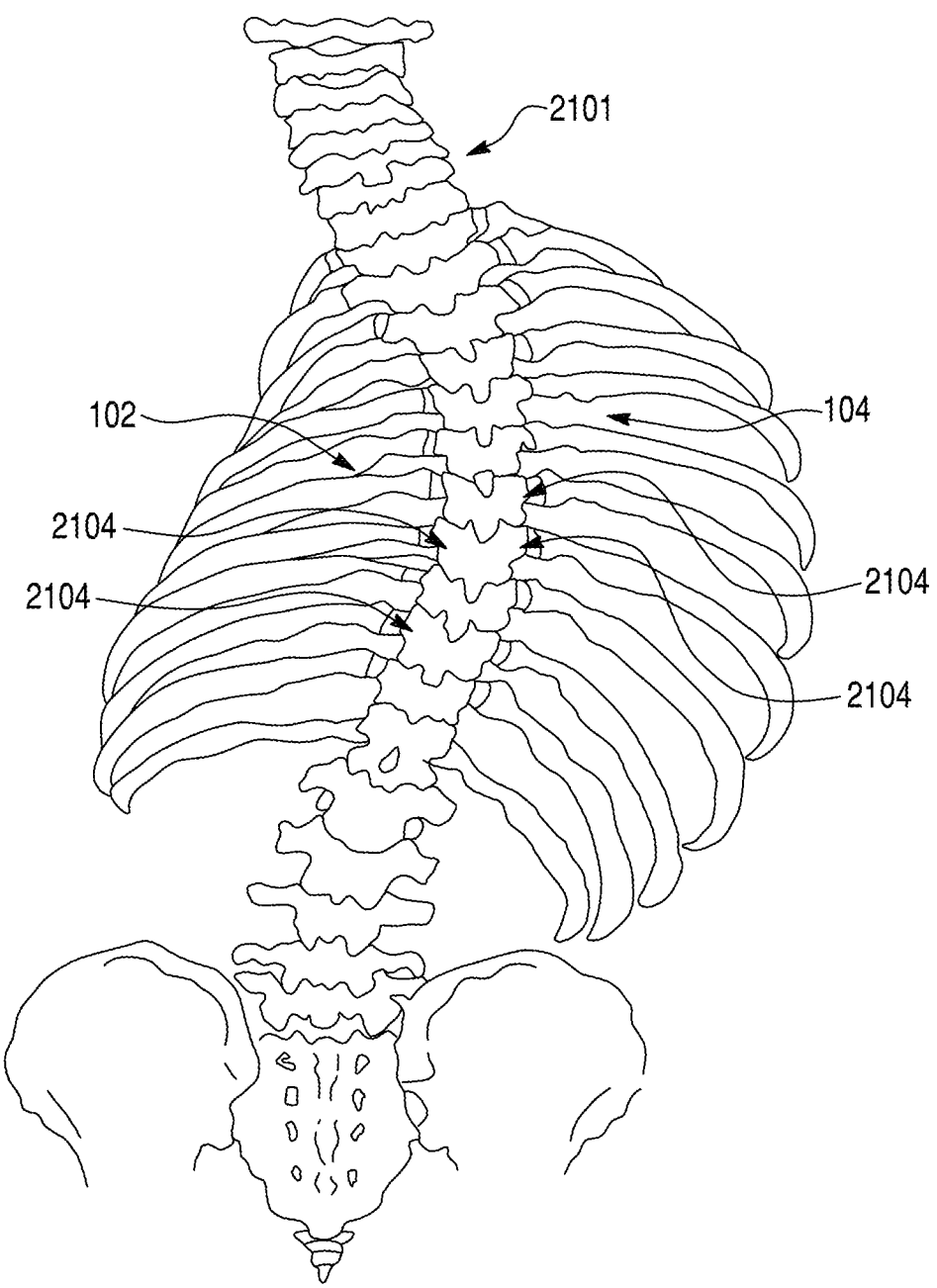
FIG. 4 is a back view of a human scoliotic spine.

A spine 2101 with an abnormal curvature along the length of the spine 2101 (due to, for example, scoliosis) is shown in FIG. 4. For example, the spine 2101 shown in FIG. 4 has a concave aspect 102 and a convex aspect 104. The screw-clamp apparatus or device 2000 may be used to correct the abnormal curvature of a spine 2101 by clamping to at least a portion of the spine 2101 with multiple screw-clamp devices 2000 connected by a rod 2051 to realign or correct the spine 2101 along its length.

Figure 5:
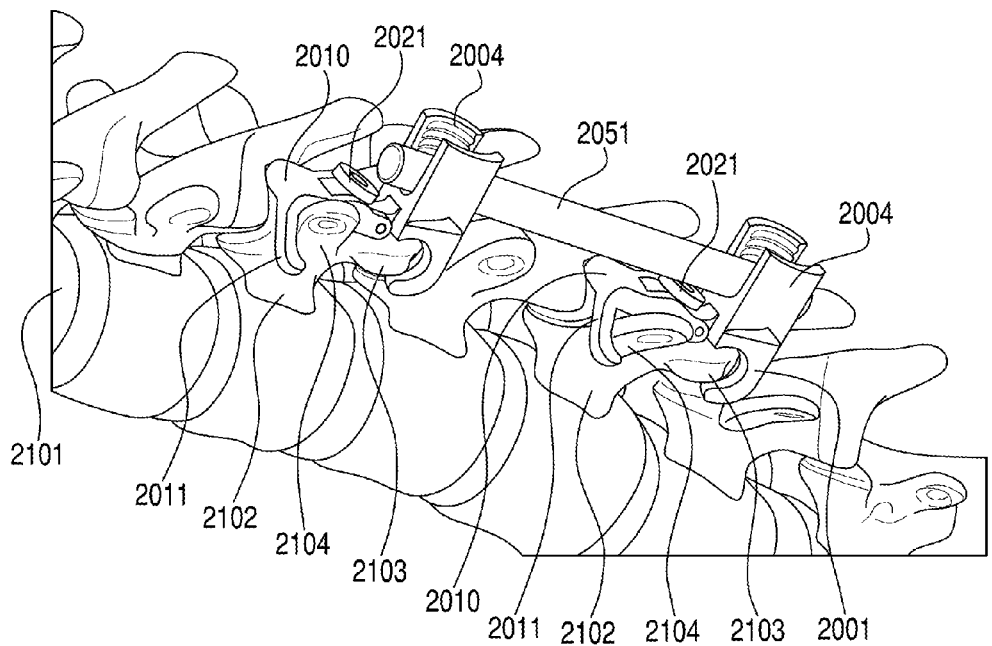
FIG. 5 is a perspective view of screw-clamp devices interconnected by a connecting rode and engaged with a human spine according to one embodiment of the present invention.

FIG. 5 illustrates an embodiment in which multiple or a plurality of screw-clamp devices 2000 are attached to and engaged with a spine 2101 and interconnected by rod 2051, in accordance with an exemplary embodiment. The screw-clamp devices 2000 may be positioned and connected along a lengthwise or longitudinal direction of the spine 2101 such that the rod 2051 may span at least a portion of the length of the spine 2101. As described in more detail below, the screw-clamp devices 2000 may clamp around a portion of bone of the spine 2101, such as parts of the vertebrae 120, and may further be screwed into the spine 2101.

The screw-clamp devices 2000 can be connected over multiple segments of the thoracic spine or vertebrae 114. However, it is anticipated that the screw-clamp devices 2000 may attach to vertebrae 120 along any region of the spine 2101. For example, the screw-clamp device 2000 is configured to fit to the spine as shown in FIG. 5 with the clamp arm/rod-receiver portion (clamp component 2001) hooking into the spinal facet joints 2103 and the proximal "claw" clamp components 2010 closing around the laminas (not shown) with the medial downward hook 2012 and around the transverse process 2104 with the lateral oblique downward hooks 2011. Alternatively or additionally, at least one of the clamp components 2001, 2010 may attach to a lateral mass of the vertebrae. In FIG. 5, the proximal clamp component 2010 (toward the head) is left and is asymmetrical, as shown according to the illustrated embodiments. However, it is anticipated that hooks 2002 and hooks 2011 and 2012 may be configured to attach to other portions or segments of the vertebrae 120.

Small bone screws 2020 may be directed towards or screwed into pedicles 2102 (which may be disposed below screw-clamp device 2000 according to the screw-clamp device's positioning and orientation), causing the claw constructs (e.g. screw-clamp device 2000) to close snugly around the bilateral masses or bone. The "tulip" or u-shaped portion (rod-receiver 2004) of the clamp components 2001 may allow screw-clamp devices 2000 to connect to rod 2051 to connect multiple screw clamp devices 2000 along the length of the spine 2101. The rod-receiver 2004 may allow screw-clamp devices 2000 to connect to rod 2051 and to connect with multiple other devices such as conventional hooks or pedicle screws.

Figure 6A:
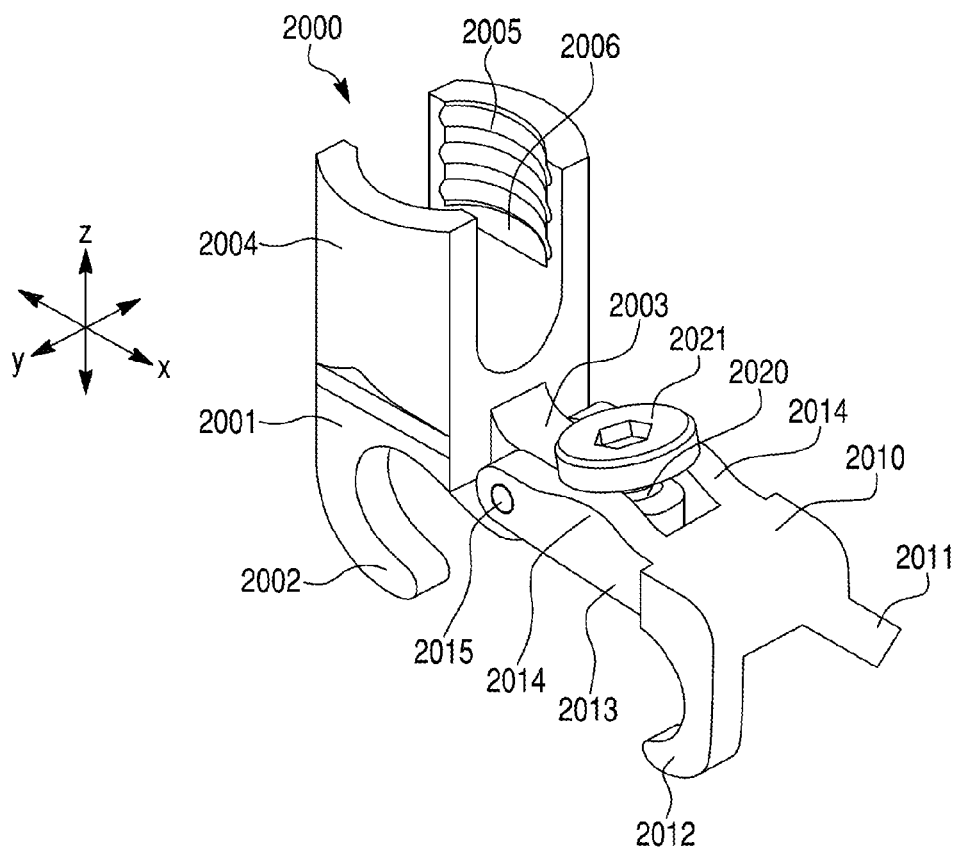
FIG. 6A is a perspective view of the screw-clamp device of FIG. 5.
Figure 6B:
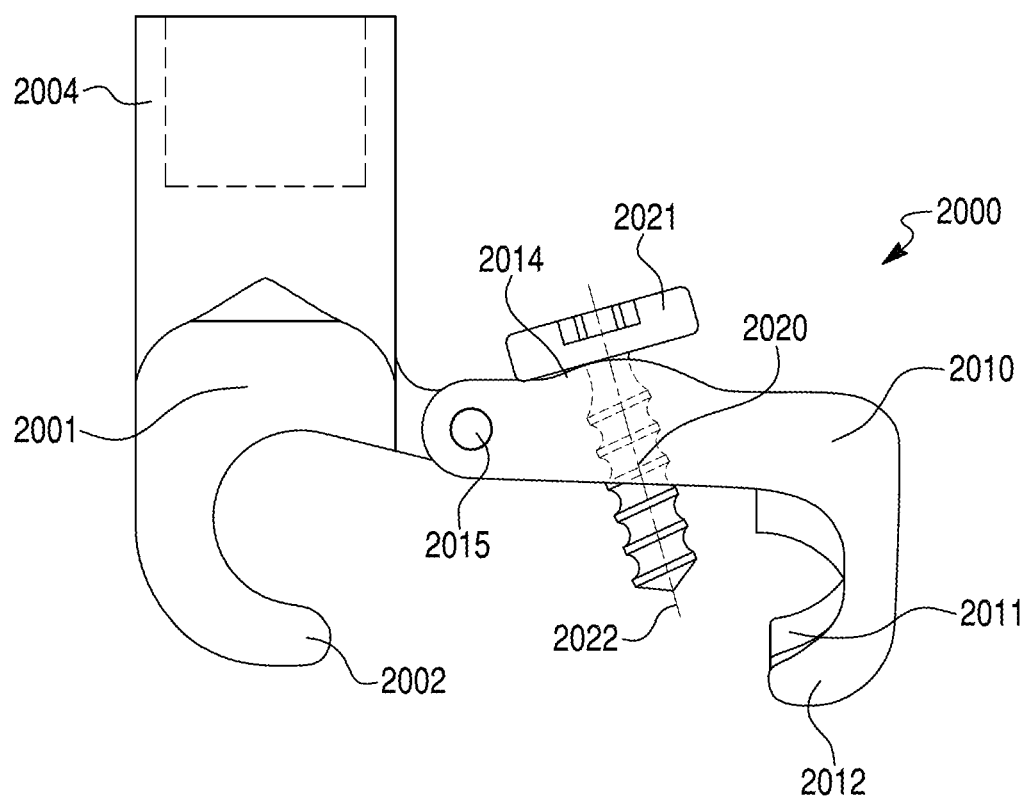
FIGS. 6B-6D are side, rear (back), and top wire-frame depictions, respectively, of the screw-clamp device of FIG. 5.
Figure 6C:
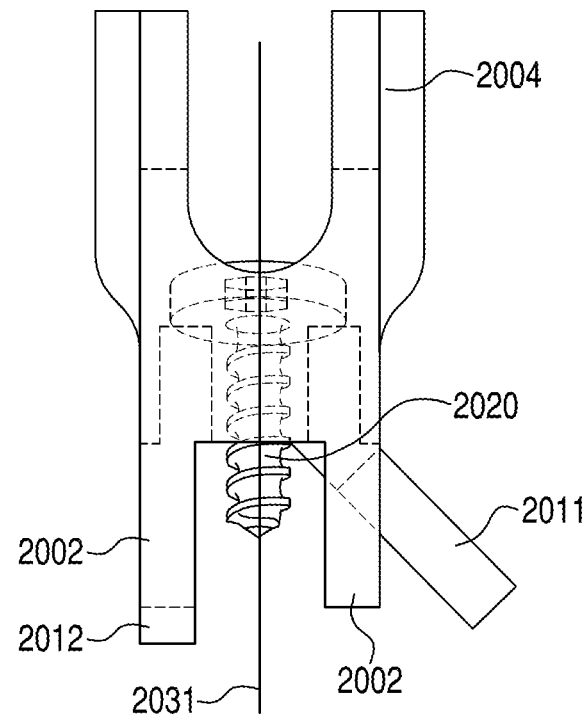
Figure 6D:
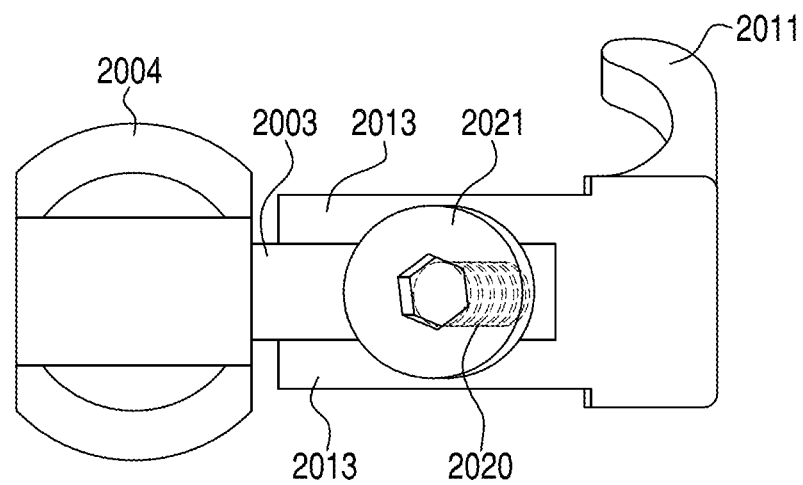

FIG. 6A is a perspective view of a screw-clamp device 2000 in accordance with an exemplary inventive embodiment. The screw-clamp device 2000 has a first or distal clamp component, clamp component 2001, with at least one hook 2002 to attach to or hook at least partially around bone. A second or proximal clamp component, clamp component 2010, may be hingeably or pivotably attached to the clamp component 2001 and may also have at least one hook 2011 and/or 2012 to attach to or hook at least partially around bone, as shown in FIG. 5. As shown in FIGS. 6B-6D, bone-screw hole or guide 2181 may be located at least partially within the clamp component 2001 such that a bone screw 2020 may be inserted therein to engage with the second clamp component 2010. The bone screw 2020 may be screwed at least partially through the clamp component 2001 and into bone. As shown in FIGS. 8A-8C and discussed in more detail below, as the bone screw 2020 is tightened within or inserted into the bone-screw hole 2181, or advanced into underlying bone, the bone screw 2020 may cause the second clamp 2010 to pivot toward the first clamp component 2001, thereby tightening the grip of the screw-clamp device 2000 on the bones between the hooks 2002 and hooks 2011 and 2012. As shown in FIG. 5 and discussed in more detail below, the first clamp component 2001 may additionally include a spacer- or rod-receiver 2004, which may be configured to secure a rod 2051 to the clamp component 2001. The rod 2051 may additionally be connected to at least one other screw-clamp device 2000 such that the multiple screw-clamp devices 2000 and the rode 2051 are aligned along the lengthwise direction of a spine.

As shown in FIG. 7, the first or distal clamp component, clamp component 2001 may have at least one up-going hooks, hooks 2002. Hooks 2002 may fit into, attach to, or hook at least partially around a bone. For example, hooks 2002 may hook around a portion of the spine, such as a facet joint 2103 on the vertebrae 120. Hooks 2002 may also attach to a bone graft.

In some embodiments, clamp component 2001 may include at least one up-going hook 2002. The hook 2002 may be extend from any portion of the clamp component 2001. For example, the at least one hook 2002 may extend from the clamp component 2001 along the vertical direction or z-axis and may further extend at least partially along the longitudinal direction or x-axis. The hook 2002 may further extend at least partially back into the z-axis along the length of the hook 2002, such that the hook 2002 generally makes a "C" shape. Optionally, the hook 2002 may extend at least partially along the lateral direction or y-axis. The hook 2002 may be curved or may include straight segments.

Figure 7A:
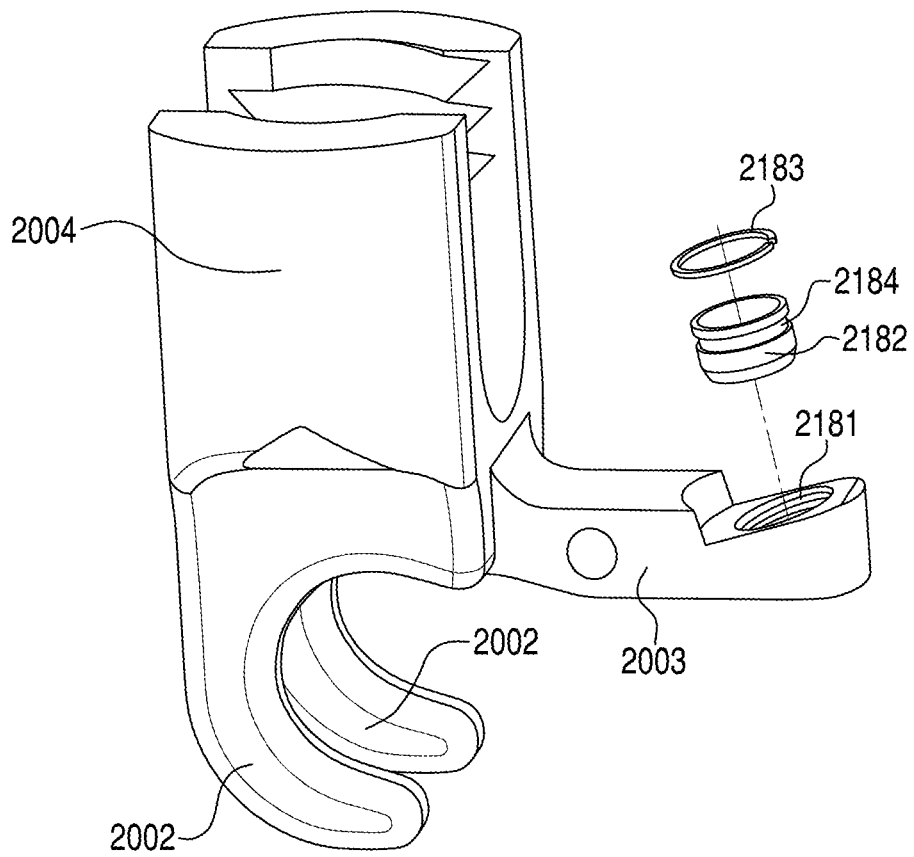
FIGS. 7A-7B illustrate perspective, exploded views of the clamp component of the screw-clamp device of FIG. 5 including a bushing, c-clip and a screw guide for fitting a bone screw therein.
Figure 7B:
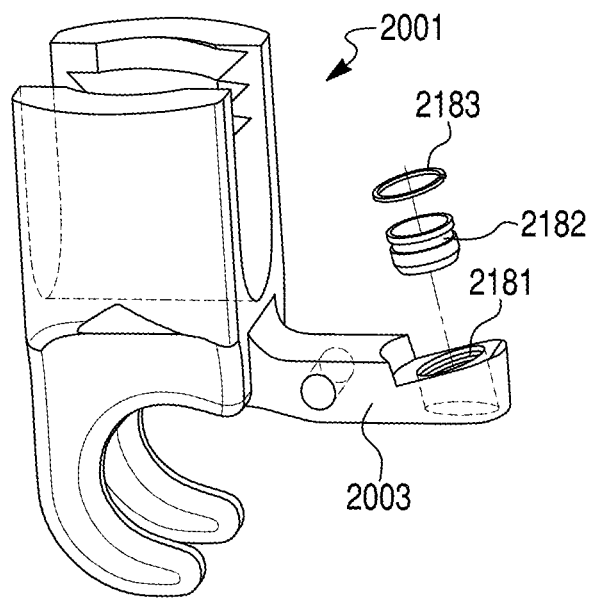
Figure 7C:
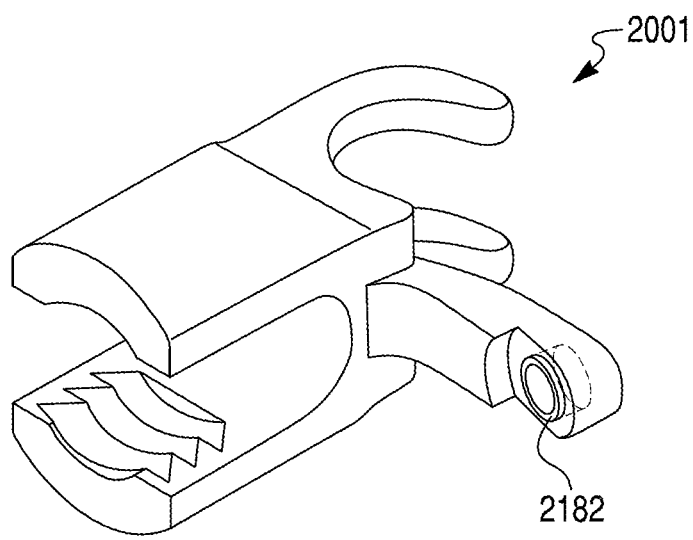
FIGS. 7C-7D illustrate a perspective angled view and a front view, respectively, of the clamp component of FIG. 7A.
Figure 7D:
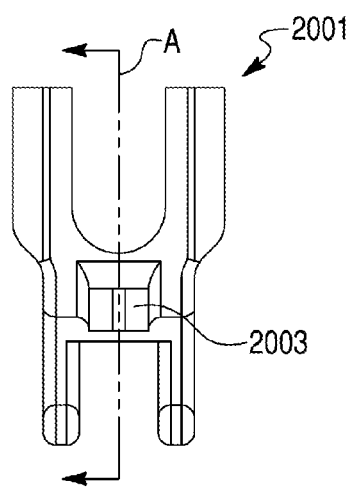
Figure 7E:
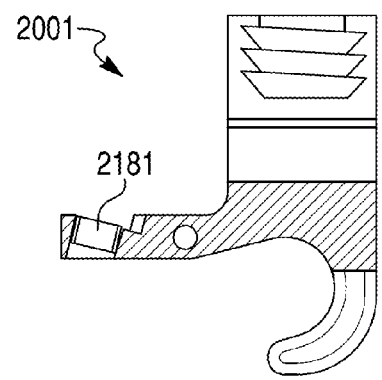
FIGS. 7E and 7F are cross-sectional, side views of the clamp component of FIG. 7A through axis A of FIG. 7D.
Figure 7F:
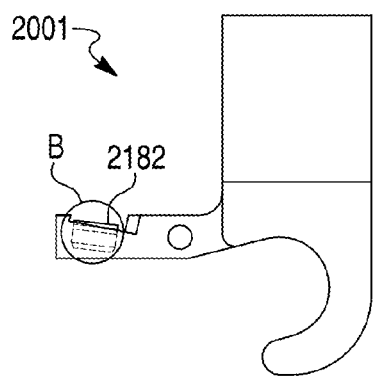
Figure 7G:
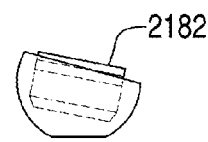
FIG. 7G is a side view of a screw guide and bushing of the clamp component of FIG. 7A from section B of FIG. 7F.

The clamp component 2001 may have any number of hooks, according to the desired configuration. As shown in FIGS. 7A and 7D, the clamp component 2001 may have two hooks 2002. However, it is anticipated that the clamp component 2001 may only have one hook 2002, which may be located anywhere along the clamp component 2001, such as along the longitudinal midline of the clamp component 2001.

In the illustrated embodiment in FIG. 7D, clamp component 2001 is a symmetrical component with respect to a midline extending between hooks 2002 as will be demonstrated further herein. The hooks 2002 may further be parallel to each other. However, it is anticipated that the hooks 2002 may be asymmetrical about a longitudinal midline of the clamp component 2001.

As shown in the illustrated embodiment of FIG. 6A, the second or proximal hinged clamp component 2010 also has dual hooks (similar to the hooks 2002 of the first clamp component 2001), including medial down-going hook 2012 configured to engage the lamina and a lateral down-going hook 2011, extending, at least in part, in a lateral direction with respect to clamp component 2010. The hooks 2011, 2012 may be sized or oriented according to the desired configuration. For example, it may be desirable for the hooks 2011, 2012 to attach to other bones or portions of the vertebrae 120. In the illustrated embodiment, clamp component 2010 is an asymmetrical clamp component with respect to a midline extending between hooks 2011 and 2012 (along the longitudinal axis).

As depicted in FIG. 6C, lateral hook 2011 extends in a lateral direction from clamp component 2010, while hooks 2002 and hook 2012 extend downwardly from the clamp components in the vertical direction. The lateral extension of lateral hook 2011 is also illustrated in FIG. 6D. Accordingly, clamp component 2010 is asymmetrical with respect to a midline 2031.

Hooks 2002 and hooks 2011, 2012 may be positioned or oriented such that the hooks open up toward each other to allow the screw-clamp device 2000 to clamp at least partially around bone between the hooks. It is anticipated that the clamp component 2001 and the hooks 2011 and 2012 may be configured or shaped according to the desired configuration, similar to that of the clamp component 2010 and hooks 2002.

As shown in FIGS. 8A-8C, clamp component 2001 may be rotatably or pivotally attached or coupled to clamp component 2010. In the illustrated embodiment and as shown in FIGS. 7A-7D and 7H, clamp component 2001 may include a clamp arm 2003 to movably attach with at least one arm 2013 of the clamp component 2010, as shown in FIG. 6A. FIG. 6D clearly shows how arm 2003 of clamp component 2001 may be positioned between clamp arms 2013 of clamp component 2010, in the illustrated embodiment. The clamp components 2001 and 2010 may be pivotally attached along the clamp arms 2003 and 2013 toward an "attachment end." The attachment end may be on the opposite end (along the longitudinal axis of the clamp components 2001 and 2010) as where the respective hooks 2002, 2011, 2012 extend from (e.g. the "hook end") on the clamp components 2001 and 2010. For example, the hook ends the clamp components 2001 and 2010 may be on an outside portion of the screw-clamp device 2000 while the attachment ends the clamp components 2001 and 2010 may be in the middle of the screw-clamp device 2000.

The clamp components 2001 and 2010 may be rotatably coupled through a variety of different mechanisms. For example, as shown in FIGS. 6A and 9, clamp component 2001 may be rotatably attached to clamp component 2010 via pin 2015 extending through arms 2013 of clamp component 2010 and arm 2003 of clamp component 2001 along the y-axis, such that the clamp components 2001 and 2010 may rotate with respect to each other along the x-axis and z-axis. As FIG. 9 shows, arms 2003 and 2013 of clamp components 2001 and 2010 respectively include apertures for receiving pin 2015 for rotatable coupling.

Clamp arm 2003 may be configured for engagement with screw 2020 (such as a bone screw) via a bone-screw guide 2181 as discussed further herein. In the illustrated embodiment and as shown in FIG. 9, clamp component 2001 may be configured to receive bone screw 2020, within arm 2003 of clamp component 2001. The bone-screw guide 2181 may be located anywhere along the length of the clamp component 2010. As shown in FIGS. 7A and 9, the bone-screw guide 2181 may be located on the opposite end as the hooks 2002 (along the x-axis).

Figure 7H:
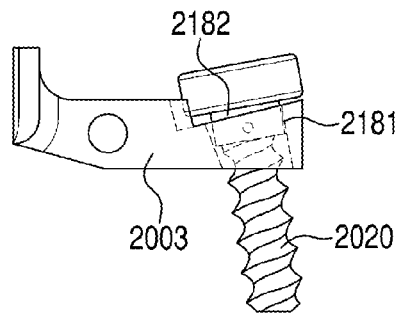
FIG. 7H is a side view of an arm of the clamp component of FIG. 7A with a screw, including a screw guide and a bushing for fitting therein, in accordance with an exemplary embodiment.

FIGS. 7A-7H illustrate clamp component 2001 and arm 2003 of clamp component 2001 having a screw guide, hole, or aperture 2181 and a guide or bushing 2182 for fitting therein, in accordance with an exemplary inventive embodiment. As shown in FIG. 9, arm 2003 may be configured to receive a guide or bushing, such as bushing 2182, in connection with engagement of arm 2003 with bone screw 2020. The bone screw 2020 may advance through the bone-screw guide 2181 and into a bone. FIG. 7H illustrates a side view of a portion of the clamp arm 2003 including a bone screw 2020 within a screw guide 2181 fitted with a bushing 2182, in accordance with an exemplary embodiment.

Figure 10A:
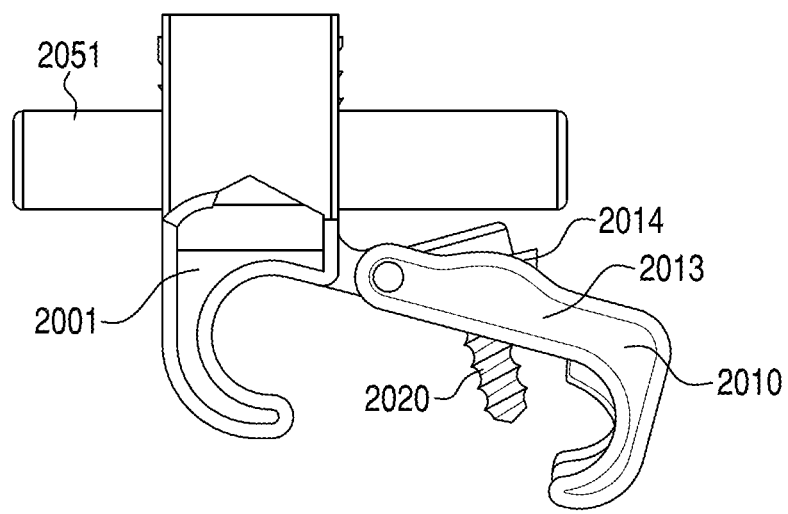
FIGS. 10A-10F provide a side, partially-sectional side, top end, sectional side, bottom end, and top views, respectively, of the screw-clamp device of FIG. 5 engaged with a connecting rod, in accordance with an exemplary embodiment.

The bone-screw guide, hole, or aperture in arm 2003 for bone screw 2020 may simply be a hole (unthreaded) in some embodiments, may be threaded (which locks the relative position of the clamp arms), or may not even exist to allow the surgeon to "free-hand" the placement of the bone screw. As shown in FIG. 10D, the guide for the bone screw 2020 may just be an unthreaded hole 2111 for guiding the angular position of screw 2020 with, for example, a bushing to secure or engage the screw 2020 or to impede the rotation of the screw 2020. Alternatively, as shown in FIG. 11, the screw-clamp device 2000 may include a threaded bone-screw guide 2141 in clamp component 2001 for engagement with bone screw 2020. The guide or aperture in arm 2003 for receiving and engaging bone screw may extend at least partially along the x-axis and the z-axis and may be angulated, for example at angle 2061 with respect to a plane of clamp component 2010 (in a proximal direction as demonstrated in FIG. 10B) to avoid neuroforamina.

Figure 10B:
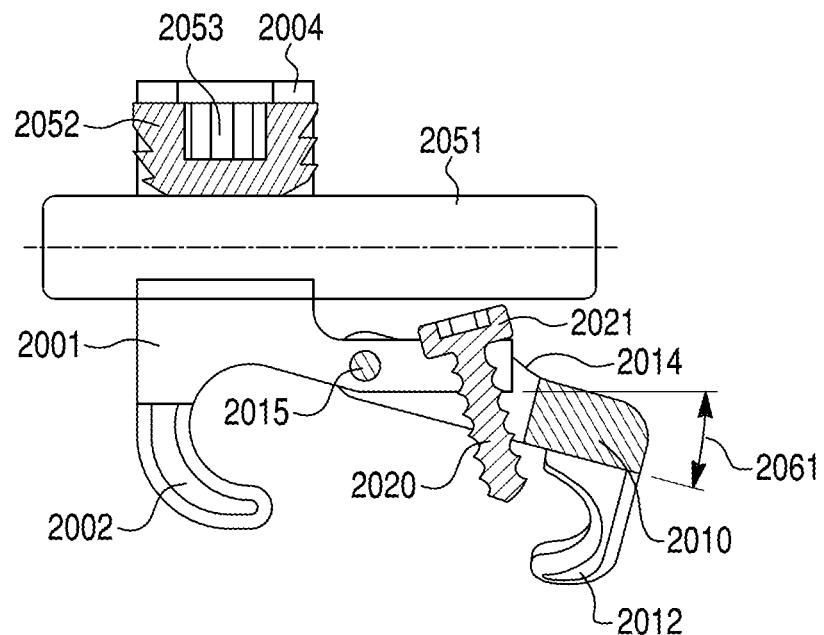
Figure 11:
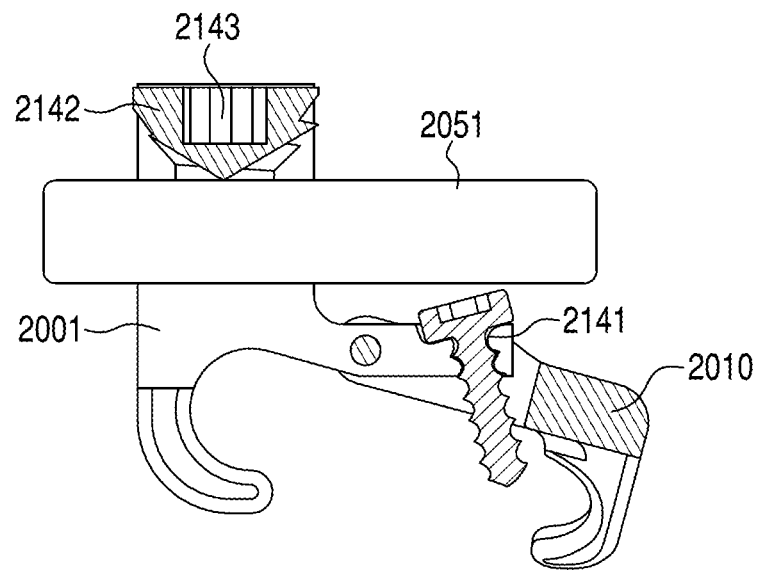
FIG. 11 illustrates a partially-sectional view of a screw-clamp device including a threaded guide for a bone screw, in accordance with an exemplary embodiment.

In accordance with various embodiments, FIG. 10B further demonstrates that bone screw 2020 may be received at an angle, including but not limited to an angle of 10 degrees, with respect to arm 2003 of clamp component 2001 to facilitate positioning of the clamp components 2001 and 2010 with respect to a bone disposed between hooks 2002 and hooks 2011, 2012 of clamp components 2001 and 2010, respectively.

The screw guide 2181 may also include a c-clip 2183 with the bushing 2182. FIGS. 7A and 7B provide a magnified, exploded view of clamp component 2001, bushing 2182, and c-clip 2183. The screw guide 2181 may have bushing 2182 to allow the screw 2020 to tilt, rotate, pivot, or swivel relative to the screw guide 2181 in the sagittal plane (which utilizes a pin) or in a polar fashion so that the screw 2020 is semi-constrained in its direction when inserted into bone. The c-clip 2183 may fit in groove 2184 on the outer aspect of bushing 2182 and a groove on the inner aspect of the screw guide 2181 in arm 2003 of clamp component 2001. The grooves are slightly oversized relative to the c-clip 2183 so that bushing 2182 may rotate and tilt within screw guide 2181 of arm 2003, which may allow the positioning and orientation of the screw 2020 within the screw guide 2181 to be adjusted. Bushing 2182, which is illustrated in FIG. 7A as un-threaded, may be threaded in some embodiments.

FIGS. 8A-8C illustrate a screw-clamp device 2000 in various positions related to transitioning from an open state to a closed state as the clamp components 2001 and 2010 pivot with respect to each other, in accordance with an exemplary inventive embodiment. FIG. 8A shows screw-clamp device 2000 in an open or extended position. The screw-clamp device 2000 may be at least partially attached to a bone within the body while in the open position. According to one embodiment, the clamp component 2001 may be first attached to the bone before clamp component 2010. FIG. 8B shows screw-clamp device 2000 in a partially closed position, as clamp component 2010 rotates counter-clockwise about pin 2015 with respect to clamp component 2001. The bone screw 2020 may help or cause the clamp component 2010 to pivot toward the clamp component 2010 by pressing on a surface of the clamp component 2010 as the screw 2020 is screwed into the screw guide 2181 and into the bone. As discussed in more detail below, a rod 2051 may be positioned in rod-receiver 2004 of clamp component 2001 as the screw-clamp device 2000 is moved from the open position to the closed position. FIG. 8C shows screw-clamp device 2000 in a further closed position, as bone screw 2020 descends further into clamp component 2001 (and may be at least partially inserted into a bone), causing clamp component 2010 to rotate further counterclockwise (in the depicted orientation) and clamp around bone. As the screw-clamp device 2000 moves from the open position to the closed position, the space between clamp components 2001 and 2010 (and their respective hooks) decreases, thereby increasing the amount of hold the screw-clamp device 2000 has on the bone secured between the hooks.

As described previously, the screw 2020 may cause the clamp component 2010 to rotate with respect to the clamp component 2001. As screw 2020 is advanced downwardly, for example along its longitudinal axis 2022 (with respect to the length of the screw 2020, as shown in FIG. 6B), clamp component 2010 is forced to rotate clockwise about pin 2015 such that the space between hooks 2002 and hooks 2011, 2012 is decreased, thereby tightening the grip or hold that screw-clamp 2000 has on any bone disposed there between. The tightening provided allows screw-clamp device 2000 to act in a claw-like manner on a bone, independent of securing a rod 2051 in the screw-clamp device 2000. Additionally, if screw 2020 bottoms out, the securing and orientation of the rod 2051 (that may be secured in screw-clamp device 2000) is not impacted.

Clamp arms 2013 may include cam surfaces, a prominence, a protruding portion, or shoulders 2014 shaped and positioned to cause clamp component 2010 to rotate upon application of force (by, for example, the screw 2020) to cam surfaces 2014. Screw-clamp device 2000 is configured such that a portion (such as the head) of screw 2020 may engage with a portion of the screw-clamp device 2000. As demonstrated in FIGS. 6B, 8A, and 10B, screw head 2021 may abut a cam shoulder 2014 of clamp component 2010 as the screw 2020 is inserted or screwed into the screw guide 2181. As screw 2020 screws and/or advances into the screw guide 2181 and a bone, the head 2021 of screw 2020 may apply a force on a shoulder or cam surface 2014 of clamp arms 2013, causing the clamp components 2001 and 2010 to simultaneously close toward each other with respect to one another. In the illustrated embodiment, screw 2020 (or screw head 2021) abuts cam surface or shoulder 2014 on arm 2013 of asymmetric clamp component 2010, causing or forcing the clamp component 2010 to pivot or rotate toward the clamp component 2001 while the clamp component 2001 may remain stationary (with respect to the bone(s) the clamp component 2001 is at least partially secured around). In various embodiments, the cam surface 2014 may be disposed on the symmetrical clamp component 2001 and the screw guide 2181 may be disposed on the asymmetrical clamp component 2010.

Figure 13:
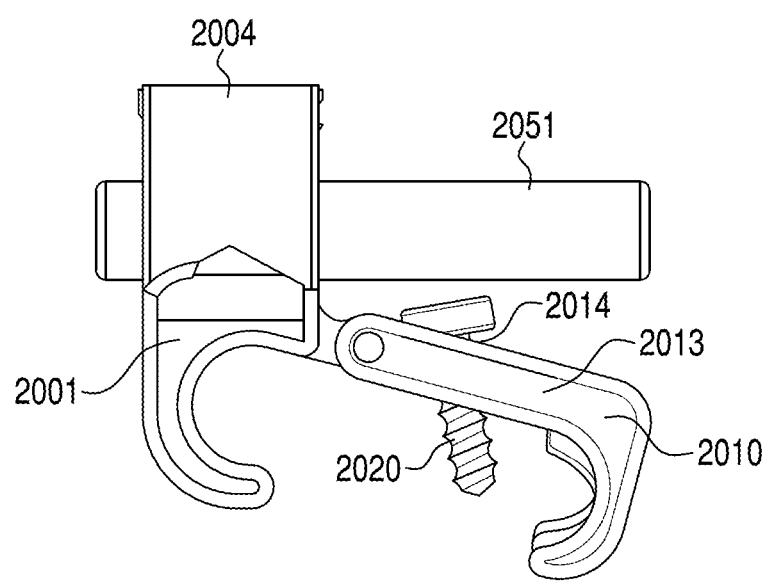
FIG. 13 illustrates a side view of a screw-clamp device with a recessed cam surface, in accordance with an exemplary embodiment.

As shown in FIGS. 10A and 13, the cam surfaces 2014 may be shaped according to the desired configuration. For example, the cam surfaces 2014 in FIG. 10A is substantially flat, while the cam surfaces 2014 in FIGS. 6A and 13 are at least partially rounded. The cam surfaces 2014 may engaged with the head 2021 of the screw 2020. Alternatively or additionally, the head 2021 may be at least partially recessed within the clamp arms 2013 as shown in FIG. 13.

As further illustrated in FIG. 6A, clamp component 2001 may include a u-shaped spacer-receiver or rod-receiver 2004 positioned atop or capping clamp component 2001. Alternatively, rod-receiver 2004 may be positioned atop clamp component 2010 in various embodiments. Rod-receiver 2004 may be integrally formed as a part of clamp component 2001. Rod-receiver 2004 may be positioned above arm 2003, such that while the screw 2020 is engaged in arm 2003, the screw 2020 may be located below a spacer or rod secured within the rod-receiver 2004, as will be demonstrated further herein. Rod-receiver 2004 may include a plurality of threads 2005 and a base 2006 disposed at a distance above the inner lowest surface or platform of the u-shaped rod-receiver, such that a retaining member (engaged in the rod-receiver) may securely maintain a rod within the rod-receiver 2004.

As depicted in FIG. 9, clamp component 2001 may be structured to receive a connecting spacer or rod 2051, and a retaining member, spacer-securing component, or rod-securing component, such as set screw 2052, for maintaining rod 2051 in rod-receiver 2004 of clamp component 2001, as will be demonstrated further herein.

Figure 10C:
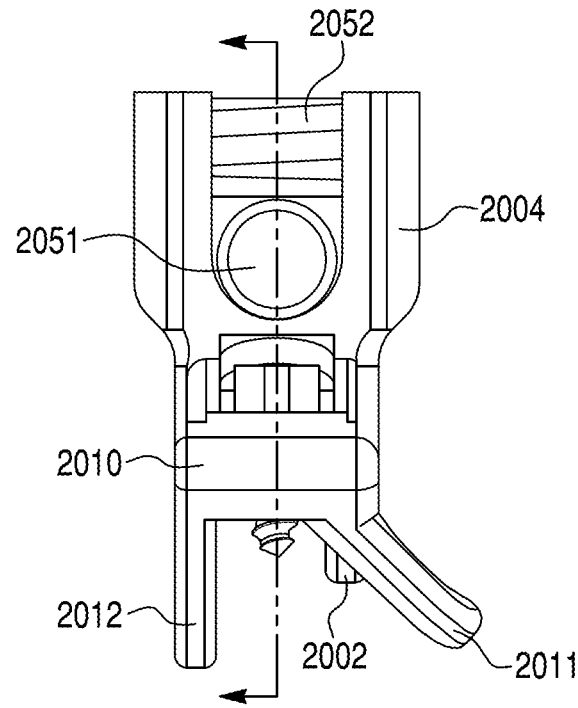
Figure 10D:
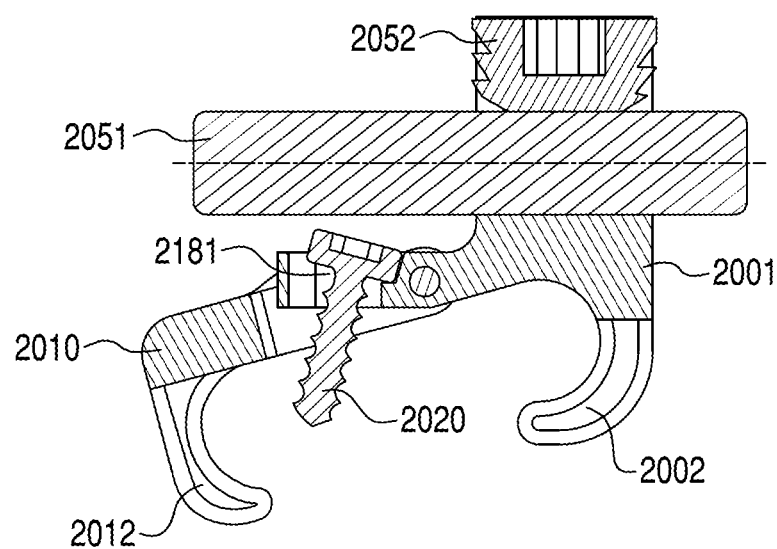
Figure 10E:
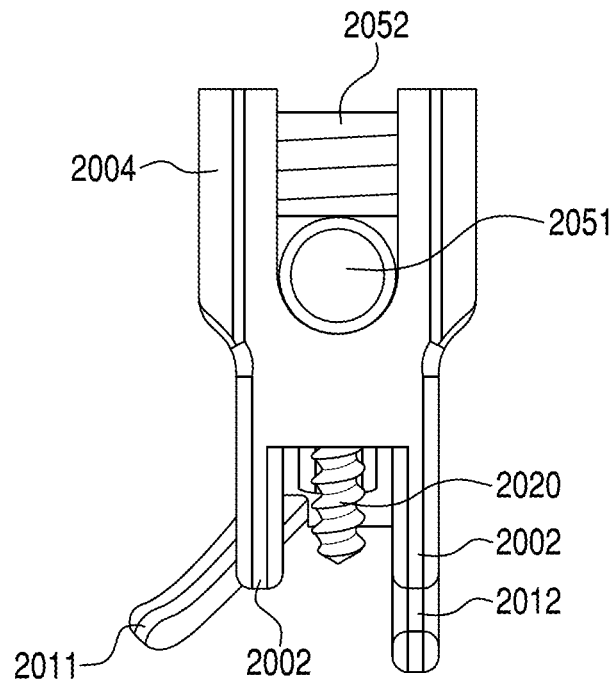
Figure 10F:
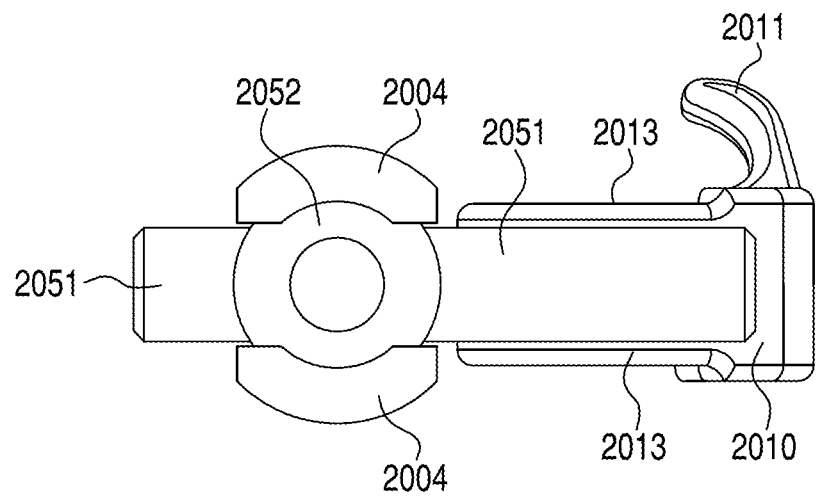

The screw-clamp 2000 may be engaged with connecting rod 2051, in accordance with an exemplary embodiment. As shown in FIGS. 10A-10F, the rod 2051 may be secured along the longitudinal axis of the screw-clamp device 2000 above the screw 2020 and within the rod-receiver 2004. FIG. 10C demonstrates the engagement of engagement member or set screw 2052 with rod 2051 according to one embodiment. As shown in FIGS. 10B-10E, screw 2052 may maintain rod 2051 in the u-shaped channel of rod-receiver 2004 of clamp component 2001, between clamp component 2001 and screw 2052. Screw 2052 may be screwed, attached, or secured within the rod-receiver 2004, on top of the rod 2051 and may be removably engagable with the rod-receiver 2004. Screw 2052 may include a keyed recess 2053 shaped to receive a tool, such as an hex key, for applying torque to screw 2052 for engagement with rod-receiver 2004.

As shown in FIGS. 10B and 10D, the screw 2052 is depicted as having a planar bottom surface for engaging rod 2051. However, the screw 2052 may include other geometries in accordance with inventive embodiments disclosed herein. For example, FIG. 11 depicts an alternative engagement screw 2142, which may be comparable to screw 2052. As demonstrated in FIG. 11, the engagement screw 2142, configured for engaging and securing rod 2051, may have alternative geometries such as a pointed base and, like screw 2052, screw 2142 may include a keyed recess 2143 shaped to receive a tool for applying torque to screw 2142 for engagement with rod-receiver 2004.

Figure 12:
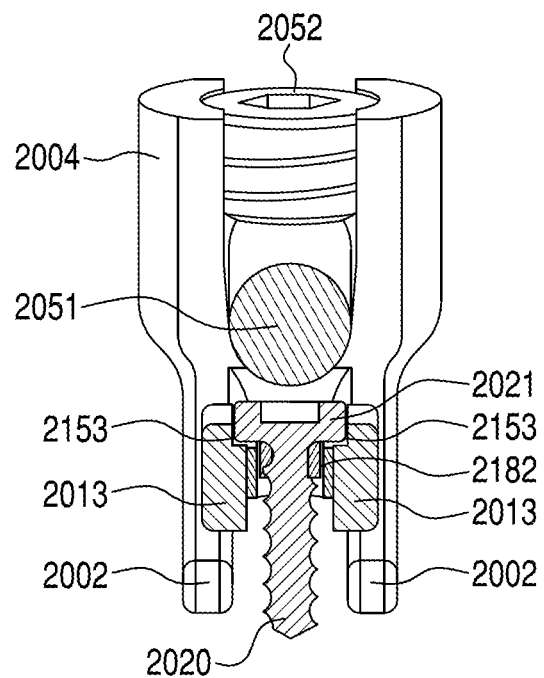
FIG. 12 illustrates a sectional, end view of a screw-clamp device fitted with a bushing and including a recessed cam surface, in accordance with an exemplary embodiment.

In order for the screw 2020 to be fully engaged with the screw-clamp device 2000 without preventing the rod 2051 from being attached to the screw-clamp device 2000, a portion of the clamp arm 2013 may be recessed to allow a screw head 2021 of the screw 2020 to at least partially recess within and at least partially abut an inner surface of the clamp arm 2013. For example, FIG. 12 illustrates a cam surface 2153 disposed in a recess within clamp arm 2013. FIG. 13 illustrates an exterior, side view of a screw-clamp device 2000 with a recessed cam in accordance with an exemplary embodiment. Positioning cam surface 2153 on the inside of proximal clamp arm 2013 permits screw head 2021 to sit recessed within clamp arm 2013 and thereby have a lower profile to avoid interference with rod 2051. The radius of curvature of the cam surface 2153 may vary depending on the desired mechanical advantage. As shown in FIGS. 12 and 13, the cam surface 2153 may be at least partially hidden or concealed within the screw-clamp device 2000.

As demonstrated in FIGS. 10A-10F, clamp component 2001 of screw-clamp device 2000 is configured such that bone screw 2020 may be positioned between connecting rod 2051 and clamp component 2001 in the engaged positioned (e.g in the closed position). Accordingly, the rod 2051 may further assist with preventing bone screw 2020 from backing out of the bone, displacing, loosening, retracting out of the bone or the screw-clamp device, becoming lost within the body, and detaching the screw-clamp device 2000 from the bone.

According to another embodiment, clamp components 2001 and 2010 may be integrally formed (e.g. manufactured as a single component) with arms 2003 and 2013, respectively. However, it is anticipated that the clamp components 2001 and 2010 may be separate from and attachable or connectable with the arms 2003 and 2013, respectively, during or after the manufacturing process, such that the clamp components 2001 and 2010 may be separate components from the arms 2003 and 2013, respectively. It is also anticipated that the clamps components 2001 and 2010 may be manufactured as a single, integral piece with the hooks 2002 and 2011, 2012, respectively, or may be a separate piece from the hooks 2002 and 2011, 2012, respectively, and later connected together.

The bilateral constructs of the screw-clamp device 2000, which are commonly applied during the correction of a scoliotic spine, may allow for powerful derotation maneuvers by providing a surgeon with greater leverage to perform axial rotation maneuvers via device holders or extensions that are temporarily held onto the devices acting as lever arms. For example, the bilateral constructs extend up (perpendicular) to the spinal axis and allow a surgeon to twist the spine about its long axis. In a manner similar to older hooks, the embodiments of the screw-clamp device 2000 disclosed herein may be placed under direct visualization. This contrasts with pedicle screws that require imaging at some point to assure the surgeon they are correctly placed. Unlike conventional pedicle screws, screws 2020 used with the embodiments disclosed herein (i.e. bone screw 2020) are small enough so that there is substantially no danger to the nervous structure and thus visualization of bone screw 2020 into the bone is not required.

The screw-clamp device 2000 may further allow clamp component 2001 to be first be positioned within the body (at least partially around a bone with the hooks 2002) and then the other clamp component 2001 to be subsequently pivoted and positioned within the body (at least partially around a bone with the hooks 2011, 2012). Positioning one clamp component at a time (in series, instead of in parallel at the same time) may allow the screw-clamp device 2000 to be attached and positioned easier. Further, it may be easier for the bone screw 2020 to be accurately and precisely positioned within the bone since the clamp component 2001 has already been secured and properly positioned with the bone (instead of clamping both clamp components 2001 and 2010 while screwing in the bone screw 2020). Additionally, since the clamp component 2001 may remain stationary and upright around the bone as the clamp component 2010 is pivoted, the rod 2051 may be more securely held in the rod-receiver 2004 since the rod-receiver 2004 is not tilted.

Screw-clamp apparatuses and components described herein may be composed of a material that is biocompatible and/or include a biocompatible coating on the attachment components to enhance fixation of the attachment members to bone comprised of a porous surface texture. The biocompatible coating/material can comprise, for example, hydroxyappetite. The screw-clamp apparatus embodiments may be made of different materials such that, for example, the material forming the bone screw is different than the material forming the clamp components and/or the material. In various embodiments, the screw-clamp apparatus in accordance with various inventive embodiments may be composed of materials such as, titanium, cobalt, and chrome-alloy, and stainless steel.

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of the screw-clamp or components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, describes techniques, or the like, this application controls.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. A screw-clamp apparatus comprising:
    a first clamp component comprising a first clamp component body and at least one hook extending from a first side of the first clamp component body and configured to receive a bone on the first side of the first clamp component body;
    a second clamp component comprising at least one hook, wherein the second clamp component is pivotably attached relative to the first clamp component;
    a bone-screw hole located on the first clamp component;
    a bone screw configured to be inserted through the bone-screw hole and to be inserted into bone, wherein a portion of the bone screw is configured to engage the second clamp component upon insertion to cause the second clamp component to pivot toward the first clamp component; and
    a spacer-receiver located on the first clamp component, wherein the spacer-receiver extends from a second side of the first clamp component body that is opposite to the first side, and the spacer-receiver is oriented and configured to receive and secure a spacer on the second side of the first clamp component body such that the spacer extends over the bone screw such that the spacer prevents the bone screw from loosening.

2. The screw-clamp apparatus of claim 1, wherein the second clamp component comprises at least two hooks, wherein the at least two hooks of the second clamp component are asymmetrical along a longitudinal direction through a midline of the second clamp component, wherein at least one of the two hooks of the second clamp component extends at least partially in a lateral direction.

3. The screw-clamp apparatus of claim 1, wherein the first clamp component is symmetrical about a longitudinal direction of a midline of the first clamp component.

4. The screw-clamp apparatus of claim 1, wherein the first and second clamp components are configured to attach to at least one of a facet joint, a lamina, a lateral mass, and a transverse process.

5. The screw-clamp apparatus of claim 1, wherein the first and second clamp components comprise attachment ends and hook ends, wherein the first and second clamp components are pivotally attached through the attachment ends and the hooks of the first and second clamp components are located on the respective hook ends.

6. The screw-clamp apparatus of claim 1, further comprising a spacer-securing component configured to attach the spacer to the spacer-receiver, wherein the spacer-securing component is removably engagable with the spacer-receiver.

7. The screw-clamp apparatus of claim 1, wherein the spacer is secured at least partially within the spacer-receiver along a longitudinal direction of the screw-clamp apparatus.

8. The screw-clamp apparatus of claim 1, wherein the bone-screw hole comprises a bone-screw bushing configured to allow the bone screw to tilt relative to the bone-screw hole.

9. The screw-clamp apparatus of claim 1, wherein at least one of the first clamp component and the second clamp component has a protruding portion, wherein a force applied onto the protruding portion by a bone screw-head of the bone screw pivots the second clamp component toward the first clamp component.

10. The screw-clamp apparatus of claim 1, wherein the at least one hook and the spacer-receiver each extend from the first clamp component body in opposite directions.

11. An orthopedic device to realign bone segments, the orthopedic device comprising:
at least two screw-clamp apparatus each comprising:
a first clamp component comprising a first clamp component body and at least one hook extending from a first side of the first clamp component body and configured to receive a bone on the first side of the first clamp component body,
a second clamp component comprising at least one hook, wherein the second clamp component is pivotably attached relative to the first clamp component,
a bone screw configured to be inserted into the first clamp component and into bone, wherein a portion of the bone screw is configured to engage the second clamp component upon insertion to cause the second clamp component to pivot toward the first clamp component, and
a spacer-receiver located on the first clamp component, wherein the spacer-receiver extends from a second side of the first clamp component body that is opposite to the first side; and
a spacer connecting the at least two screw-clamp apparatus along a lengthwise direction of a spine,
wherein each of the spacer-receivers are oriented and configured to receive and removably secure the spacer on each of the second sides of the first clamp component bodies such that the spacer extends over the bone screws such that the spacer prevents the bone screws from loosening.

12. The orthopedic device of claim 11, wherein the second clamp components comprise at least two hooks, wherein the at least two hooks of the second clamp components are asymmetrical along a longitudinal direction through a midline of the second clamp components, wherein at least one of the two hooks of the second clamp components extends at least partially in a lateral direction.

13. The orthopedic device of claim 11, wherein the at least two screw-clamp apparatus are configured to attach to at least one of a facet joint, a lamina, lateral mass, and a transverse process.

14. A method of assembling a screw-clamp apparatus, the method comprising:
pivotally attaching a first clamp component comprising a first clamp component body and at least one hook to a second clamp component comprising at least one hook, wherein the at least one hook extends from a first side of the first clamp component body and is configured to receive a bone on the first side of the first clamp component body;
inserting a bone screw into a bone-screw hole located on the first clamp component;
engaging the bone screw along the second clamp component to cause the second clamp component to pivot toward the first clamp component; and
attaching a spacer to a spacer-receiver located on the first clamp component, wherein the spacer-receiver extends from a second side of the first clamp component body that is opposite to the first side, and the spacer-receiver is oriented and configured to receive and secure the spacer on the second side of the first clamp component body such that the spacer extends over the bone screw such that the spacer prevents the bone screw from loosening.

15. The method of claim 14, further comprising attaching the spacer to the spacer-receiver with a spacer-receiver component removably engagable with the spacer-receiver.

16. The method of claim 14, wherein the first and second clamp components are configured to attach to at least one of a facet joint, a lamina, a lateral mass, and a transverse process.

* * * * *